US007277747B2

(12) United States Patent
Cazares et al.

(10) Patent No.: US 7,277,747 B2
(45) Date of Patent: Oct. 2, 2007

(54) ARRHYTHMIA MEMORY FOR TACHYARRHYTHMIA DISCRIMINATION

(75) Inventors: Shelley Cazares, Minneapolis, MN (US); Julie Thompson, Circle Pines, MN (US); Yayun Lin, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 59 days.

(21) Appl. No.: 10/996,340

(22) Filed: Nov. 23, 2004

(65) Prior Publication Data

US 2006/0111643 A1 May 25, 2006

(51) Int. Cl.
*A61B 5/0464* (2006.01)
(52) U.S. Cl. ...................... 600/518; 600/515
(58) Field of Classification Search ................ 600/515, 600/518
See application file for complete search history.

(56) References Cited

U.S. PATENT DOCUMENTS

| 4,023,564 | A | 5/1977 | Valiquette et al. |
|---|---|---|---|
| 4,336,810 | A | 6/1982 | Anderson et al. |
| 4,589,420 | A | 5/1986 | Adams et al. |
| 4,680,708 | A | 7/1987 | Ambos et al. |
| 4,721,114 | A | 1/1988 | DuFault et al. |
| 4,802,491 | A | 2/1989 | Cohen et al. |
| 4,809,697 | A | 3/1989 | Causey, III et al. |
| 4,825,869 | A | 5/1989 | Sasmor et al. |
| 4,830,006 | A | 5/1989 | Haluska et al. |
| 4,884,345 | A | 12/1989 | Long |
| 4,940,054 | A | 7/1990 | Grevis et al. |
| 4,947,857 | A | 8/1990 | Albert et al. |
| 4,989,610 | A | 2/1991 | Patton et al. |
| 5,000,189 | A | 3/1991 | Throne et al. |
| 5,014,698 | A | 5/1991 | Cohen |
| 5,020,540 | A | 6/1991 | Chamoun |
| 5,046,504 | A | 9/1991 | Albert et al. |
| 5,047,930 | A | 9/1991 | Martens et al. |
| 5,127,401 | A | 7/1992 | Grevious et al. |
| 5,183,040 | A | 2/1993 | Nappholz et al. |
| 5,184,615 | A | 2/1993 | Nappholz et al. |
| 5,193,535 | A | 3/1993 | Bardy et al. |
| 5,193,550 | A | 3/1993 | Duffin |
| 5,215,098 | A | 6/1993 | Steinhaus et al. |

(Continued)

FOREIGN PATENT DOCUMENTS

DE 4405827 6/1995

(Continued)

OTHER PUBLICATIONS

"Vitality 2 Implantable Cardioverter Defibrillator System Guide", *Guidant Corporation*, (2004), cover pages and pp. 3-15 to 3-19.

(Continued)

*Primary Examiner*—Carl Layno
*Assistant Examiner*—Yun Haeng Lee
(74) *Attorney, Agent, or Firm*—Schwegman, Lundberg & Woessner, P.A.

(57) ABSTRACT

This document discusses, among other things, a method of identifying a non-fatal tachyarrhythmia episode by determining a degree of similarity between the episode and a template generated from a previous tachyarrhythmia episode.

38 Claims, 10 Drawing Sheets

U.S. PATENT DOCUMENTS

| | | | |
|---|---|---|---|
| 5,217,021 A | 6/1993 | Steinhaus et al. |
| 5,240,009 A | 8/1993 | Williams |
| 5,266,554 A | 11/1993 | Suchy et al. |
| 5,269,301 A | 12/1993 | Cohen |
| 5,271,411 A | 12/1993 | Ripley et al. |
| 5,273,049 A | 12/1993 | Steinhaus et al. |
| 5,280,792 A | 1/1994 | Leong et al. |
| 5,292,348 A | 3/1994 | Saumarez et al. |
| 5,299,118 A | 3/1994 | Martens et al. |
| 5,311,873 A | 5/1994 | Savard et al. |
| 5,311,874 A | 5/1994 | Baumann et al. |
| 5,312,445 A | 5/1994 | Nappholz et al. |
| 5,313,953 A | 5/1994 | Yomtov et al. |
| 5,330,504 A | 7/1994 | Somerville et al. |
| 5,331,966 A | 7/1994 | Bennett et al. |
| 5,350,406 A | 9/1994 | Nitzsche et al. |
| 5,360,436 A | 11/1994 | Alt et al. |
| 5,366,487 A | 11/1994 | Adams et al. |
| 5,379,776 A | 1/1995 | Murphy et al. |
| 5,400,795 A | 3/1995 | Murphy et al. |
| 5,404,880 A | 4/1995 | Throne |
| 5,417,221 A | 5/1995 | Sickler |
| 5,421,830 A | 6/1995 | Epstein et al. |
| 5,447,519 A | 9/1995 | Peterson |
| 5,447,524 A | 9/1995 | Alt |
| 5,456,261 A | 10/1995 | Luczyk |
| 5,458,620 A | 10/1995 | Adams et al. |
| 5,458,623 A | 10/1995 | Lu et al. |
| 5,462,060 A | 10/1995 | Jacobson et al. |
| 5,464,433 A | 11/1995 | White et al. |
| 5,513,644 A | 5/1996 | McClure et al. |
| 5,527,347 A | 6/1996 | Shelton et al. |
| 5,542,430 A | 8/1996 | Farrugia et al. |
| 5,549,641 A | 8/1996 | Ayers et al. |
| 5,549,654 A | 8/1996 | Powell |
| 5,560,369 A | 10/1996 | McClure et al. |
| 5,605,159 A | 2/1997 | Smith et al. |
| 5,609,158 A | 3/1997 | Chan |
| 5,622,178 A | 4/1997 | Gilham |
| 5,628,326 A | 5/1997 | Arand et al. |
| 5,634,468 A | 6/1997 | Platt et al. |
| 5,645,070 A | 7/1997 | Turcott |
| 5,685,315 A | 11/1997 | McClure et al. |
| 5,713,367 A | 2/1998 | Arnold et al. |
| 5,718,242 A | 2/1998 | McClure et al. |
| 5,725,559 A | 3/1998 | Alt et al. |
| 5,730,142 A | 3/1998 | Sun et al. |
| 5,738,105 A | 4/1998 | Kroll |
| 5,749,900 A | 5/1998 | Schroeppel et al. |
| 5,755,739 A | 5/1998 | Sun et al. |
| 5,779,645 A | 7/1998 | Olson et al. |
| 5,782,888 A | 7/1998 | Sun et al. |
| 5,788,717 A | 8/1998 | Mann et al. |
| 5,792,065 A | 8/1998 | Xue et al. |
| 5,792,066 A | 8/1998 | Kwong |
| 5,795,303 A | 8/1998 | Swanson et al. |
| 5,797,399 A | 8/1998 | Morris et al. |
| 5,817,027 A * | 10/1998 | Arand et al. ............... 600/515 |
| 5,817,133 A | 10/1998 | Houben |
| 5,819,007 A | 10/1998 | Elghazzawi |
| 5,827,197 A | 10/1998 | Bocek et al. |
| 5,855,593 A | 1/1999 | Olson et al. |
| 5,857,977 A | 1/1999 | Caswell et al. |
| 5,873,897 A | 2/1999 | Armstrong et al. |
| 5,944,744 A | 8/1999 | Paul et al. |
| 5,951,484 A | 9/1999 | Hoium et al. |
| 5,961,467 A | 10/1999 | Shimazu et al. |
| 6,016,442 A | 1/2000 | Hsu et al. |
| 6,091,990 A | 7/2000 | Hsu et al. |
| 6,178,350 B1 | 1/2001 | Olson et al. |
| 6,192,273 B1 | 2/2001 | Igel et al. |
| 6,212,428 B1 | 4/2001 | Hsu et al. |
| 6,221,011 B1 | 4/2001 | Bardy |
| 6,223,078 B1 * | 4/2001 | Marcovecchio ............... 607/5 |
| 6,230,055 B1 | 5/2001 | Sun et al. |
| 6,233,072 B1 | 5/2001 | Liu et al. |
| 6,233,078 B1 | 5/2001 | Harano et al. |
| 6,233,487 B1 | 5/2001 | Mika et al. |
| 6,263,242 B1 | 7/2001 | Mika et al. |
| 6,266,554 B1 | 7/2001 | Hsu et al. |
| 6,270,457 B1 | 8/2001 | Bardy |
| 6,275,732 B1 * | 8/2001 | Hsu et al. .................... 607/14 |
| 6,277,072 B1 | 8/2001 | Bardy |
| 6,280,380 B1 | 8/2001 | Bardy |
| 6,301,503 B1 | 10/2001 | Hsu et al. |
| 6,308,095 B1 | 10/2001 | Hsu et al. |
| 6,312,378 B1 | 11/2001 | Bardy |
| 6,312,388 B1 | 11/2001 | Marcovecchio et al. |
| 6,336,903 B1 | 1/2002 | Bardy |
| 6,358,203 B2 | 3/2002 | Bardy |
| 6,368,284 B1 | 4/2002 | Bardy |
| 6,370,430 B1 | 4/2002 | Mika et al. |
| 6,393,316 B1 | 5/2002 | Gillberg et al. |
| 6,398,728 B1 | 6/2002 | Bardy |
| 6,430,435 B1 * | 8/2002 | Hsu et al. .................. 600/518 |
| 6,434,417 B1 | 8/2002 | Lovett |
| 6,438,410 B2 | 8/2002 | Hsu et al. |
| 6,440,066 B1 | 8/2002 | Bardy |
| 6,449,503 B1 | 9/2002 | Hsu |
| 6,456,871 B1 | 9/2002 | Hsu et al. |
| 6,484,055 B1 * | 11/2002 | Marcovecchio ............... 607/5 |
| 6,487,443 B2 | 11/2002 | Olson et al. |
| 6,493,579 B1 | 12/2002 | Gilkerson et al. |
| 6,516,225 B1 | 2/2003 | Florio |
| 6,526,313 B2 | 2/2003 | Sweeney et al. |
| 6,611,713 B2 | 8/2003 | Schauerte |
| 6,654,639 B1 | 11/2003 | Lu |
| 6,681,134 B2 | 1/2004 | Morris et al. |
| 6,684,100 B1 | 1/2004 | Sweeney et al. |
| 6,687,540 B2 | 2/2004 | Marcovecchio |
| 6,708,058 B2 | 3/2004 | Kim et al. |
| 6,728,572 B2 | 4/2004 | Hsu et al. |
| 6,745,068 B2 | 6/2004 | Koyrakh et al. |
| 6,760,615 B2 | 7/2004 | Ferek-Petric |
| 6,766,190 B2 | 7/2004 | Ferek-Petric |
| 6,889,079 B2 | 5/2005 | Bocek et al. |
| 6,889,081 B2 | 5/2005 | Hsu |
| 6,978,177 B1 | 12/2005 | Chen et al. |
| 6,985,768 B2 | 1/2006 | Hemming et al. |
| 7,031,764 B2 | 4/2006 | Schwartz et al. |
| 7,039,463 B2 | 5/2006 | Marcovecchio |
| 7,103,405 B2 | 9/2006 | Sarkar et al. |
| 2002/0032469 A1 * | 3/2002 | Marcovecchio ............... 607/5 |
| 2002/0049474 A1 | 4/2002 | Marcovecchio et al. |
| 2002/0087091 A1 | 7/2002 | Koyrakh et al. |
| 2002/0091333 A1 | 7/2002 | Hsu et al. |
| 2002/0183637 A1 | 12/2002 | Kim et al. |
| 2002/0183639 A1 | 12/2002 | Sweeney et al. |
| 2002/0198461 A1 | 12/2002 | Hsu et al. |
| 2003/0060849 A1 | 3/2003 | Hsu |
| 2003/0083586 A1 | 5/2003 | Ferek-Petric |
| 2003/0083587 A1 | 5/2003 | Ferek-Petric |
| 2003/0100923 A1 | 5/2003 | Bjorling et al. |
| 2003/0120316 A1 | 6/2003 | Spinelli et al. |
| 2003/0181818 A1 * | 9/2003 | Kim et al. .................. 600/509 |
| 2003/0191403 A1 | 10/2003 | Zhou et al. |
| 2003/0195572 A1 * | 10/2003 | Bocek et al. .................... 607/9 |
| 2004/0010200 A1 | 1/2004 | Sweeny et al. |
| 2004/0015090 A1 | 1/2004 | Sweeney et al. |
| 2004/0082973 A1 * | 4/2004 | Kim et al. ..................... 607/9 |
| 2004/0093035 A1 | 5/2004 | Schwartz et al. |
| 2004/0111119 A1 | 6/2004 | Sarkar et al. |
| 2004/0111120 A1 | 6/2004 | Sarkar et al. |
| 2004/0111121 A1 | 6/2004 | Brown et al. |

| | | |
|---|---|---|
| 2004/0116972 A1* | 6/2004 | Marcovecchio ............... 607/14 |
| 2004/0127806 A1 | 7/2004 | Sweeney |
| 2004/0167579 A1 | 8/2004 | Sharma et al. |
| 2004/0171959 A1* | 9/2004 | Stadler et al. ............... 600/518 |
| 2004/0176694 A1 | 9/2004 | Kim et al. |
| 2005/0137485 A1 | 6/2005 | Cao et al. |
| 2005/0159781 A1 | 7/2005 | Hsu et al. |
| 2005/0192506 A1 | 9/2005 | Kim et al. |
| 2005/0256544 A1 | 11/2005 | Thompson |
| 2006/0074331 A1 | 4/2006 | Kim et al. |
| 2006/0079796 A1 | 4/2006 | Marcovecchio et al. |
| 2006/0095083 A1 | 5/2006 | Zhang et al. |
| 2006/0122527 A1 | 6/2006 | Marcovecchio |
| 2006/0155201 A1 | 7/2006 | Schwartz et al. |
| 2006/0161069 A1 | 7/2006 | Li |
| 2006/0281999 A1 | 12/2006 | Li |
| 2007/0049974 A1 | 3/2007 | Li et al. |

FOREIGN PATENT DOCUMENTS

| | | |
|---|---|---|
| EP | 0469817 | 2/1992 |
| EP | 0506230 | 9/1992 |
| EP | 0547733 | 6/1993 |
| EP | 0776630 | 11/1996 |
| EP | 0776631 | 11/1996 |
| EP | 0848965 | 6/1998 |
| WO | WO-97/39681 | 4/1996 |
| WO | WO-98/40010 | 9/1998 |
| WO | WO-98/53879 | 12/1998 |
| WO | WO-99/65570 | 12/1999 |
| WO | WO-00/10455 | 3/2000 |
| WO | WO-00/47278 | 8/2000 |
| WO | WO-0126733 A1 | 4/2001 |
| WO | WO-03047690 | 6/2003 |
| WO | WO-2006049767 A1 | 5/2006 |

OTHER PUBLICATIONS

Cazares, Shelley, "Cardiac Tachyarrhythmia Therapy Selection Based on Patient Response Information", U.S. Appl. No. 10/995,655, Filed Nov. 23, 2004, 50 pgs.

Cazares, Shelley, "Cardiac Template Generation Based on Patient Response Information", U.S. Appl. No. 10/995,704, Filed Nov. 23, 2004, 47 pgs.

Gold, Michael R., et al., "Advanced Rhythm Discrimination for Implantable Cardioverter Defibrillators Using Electrogram Vector Timing and Correlation", *Journal of Cardiovascular Electrophysiology*, vol. 13, No. 11, (Nov. 2002), pp. 1092-1097.

Kerr, Martha, "Shock Rate Cut 70% with ICDs Programmed to First Deliver Antitachycardia Pacing: Results of the PainFREE Rx II Trial", *NewsRhythms, MedScape CRM New*, www.medscape.com, (2003), 2 pgs.

Wathen, Mark S., et al., "Shock reduction using antitachycardia pacing for spontaneous rapid ventricular tachycardia in patients with coronary artery disease", *Circulation*, 104(7), (Aug. 14, 2001), pp. 796-801.

Kim, Jaeho, et al., "Blending Cardiac Rhythm Detection Processes", U.S. Appl. No. 11/089,185, Filed Mar. 24, 2005, 72 pgs.

"Invitation to Pay Additional Fees and Partial Search Report for Application No. PCT/US2005/035641, dated Mar. 1, 2006", 7 pages.

Cazares, Shelley, et al., "Arrhythima Discrimination Based on Determination of Rate Dependency", U.S. Appl. No. 11/312,280, Filed Dec. 20, 2005, 41 Pages.

Cazares, Shelly, et al., "Discrimination Polymorphic and Monomorphic Cardiac Rhythms Using Template Generation", U.S. Appl. No. 11/312,279, Filed Dec. 20, 2005, 46 Pages.

Afonso, V. X., et al., "ECG Beat Detection Using Filter Banks", *IEEE Transactions on Biomedical Engineering*, 46(2), (Feb. 1999), 192-202.

Afonso, V. X., et al., "Filter Bank-based ECG Beat Classification", *Proceedings of the 19th Annual International Conference of the IEEE, Engineering in Medicine and Biology society*, (Oct. 30-Nov. 2, 1997), 97-100.

Afonso, V. X., et al., "Filter Bank-based ECG Beat Detection", *Proceedings of the 18th Annual International Conference of the IEEE Engineering in Medicine and Biology Society*, Amsterdam, The Netherlands,(1996), 1037-1038.

Afonso, V. X., et al., "Filter Bank-based Processing of the Stress ECG", *IEEE 17th Annual Conference Engineering in Medicine and Biology Society*, 2, (Sep. 1995), 887-888.

Afonso, V. X., et al., "Multirate Processing of the ECG using Filter Banks", *Computers in Cardiology*, (1996), 245-248.

Duru, Firat, et al., "The Potential for Inappropriate Ventricular Tachycardia Confirmation Using the Intracardiac Electrogram (EGM) Width Criterion", *PACE*, vol. 22, 1999, (Jul. 1999), 1039-1046.

Grady, Thomas A., et al., "Prognostice Significance of Exercise-Induced Left Bundle-Branch Block", *JAMA*, vol. 279, No. 2, Jan. 14, 1998, 153-156.

Kinoshita, Shinji, et al., "Transient Disapperance of Complete Right Bundle Brach (BBB) During Exercise", *Journal of Electrocardiology*, vol. 29, No. 3, 1996, 255-256.

Li, Dan, "Method and Apparatus for Rate-Dependent Morphology-Based Cardiac Arrhythmia Classification", U.S. Appl. No. 11/151,567, Filed on Jun. 13, 2005, 53 pgs.

Morris, et al., "Intracardiac Electrogram Transformation: Morphometric Implications for Implantable Devices", *Journal of Electrocardiology, 29 Supplement*, (1996), pp. 124-129.

Stephany, et al., "Real-Time Estimation of Magnitude-Square Coherence for Use in Implantable Devices", *IEEE Computers in Cardiology*, (1992), pp. 375-378.

* cited by examiner

Fig. 9

ARRHYTHMIA MEMORY FOR TACHYARRHYTHMIA DISCRIMINATION

RELATED APPLICATIONS

This patent application is related to the following co-pending and commonly assigned applications: U.S. patent application Ser. No. 10/995,655, entitled "Tachyarrhythmia Therapy Selection Based On Patient Response Information," filed on Nov. 23, 2004; and U.S. patent application Ser. No. 10/995,704, entitled "Template Generation Based On Patient Response Information", filed on Nov. 23, 2004, both of which are hereby incorporated by reference.

TECHNICAL FIELD

This patent document pertains generally to administration of antitachyarrhythmia therapy, and more particularly, but not by way of limitation, to arrhythmia memory for tachyarrhythmia discrimination.

BACKGROUND

Arrhythmia is an abnormal rhythm of the heart. A tachyarrhythmia is an abnormally fast heart rhythm. A tachyarrhythmia originating in the ventricular region of the heart is called a ventricular tachyarrhythmia (VT). Ventricular tachyarrhythmia can produce symptoms of fainting, dizziness, weakness, blind spots, and potentially, unconsciousness and cardiac arrest. A tachyarrhythmia that does not originate from the ventricular region of the heart is called a supraventricular tachyarrhythmia (SVT). An SVT episode typically originates from an impulse arising in the atrium, the atrioventricular node (AV node), or the bundle of His. SVT episodes tend to be much less lethal than VT episodes.

Treatment for cardiac tachyarrhythmia can be administered by a medical device, such as a pacemaker or a defibrillator, which can be implanted in the human body. These devices can be configured to sense an intrinsic electrical heart signal and analyze the signal to determine whether a tachyarrhythmia is occurring. Such devices can also be configured to deliver antitachyarrhythmia therapy, such as electric stimulation. Improved cardiac rhythm management methods and systems are needed.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In varying examples, a morphological template can be generated from a tachyarrhythmia episode and used to identify a later episode. For example, a tachyarrhythmia episode can be detected by an implantable medical device and analyzed to determine whether the episode is a type that necessitates antitachyarrhythmia therapy. In one example, a morphological graph of a tachyarrhythmia episode is presented to a human analyst, such as a physician, and an assessment of the tachyarrhythmia episode is received from the human analyst. The assessment can, for example, include an input that indicates whether the human analyst deems the tachyarrhythmia episode is a VT episode or a SVT episode. In another example, the tachyarrhythmia episode can be analyzed by a computer to determine whether it is a VT or SVT episode. The computer can be in an implanted medical device, or external to the patient. A morphological template can be generated from the tachyarrhythmia episode and later used to identify a similar episode as it is occurring. For example, if a tachyarrhythmia episode correlates with an SVT template, an SVT can be declared, i.e. the episode can be identified as an SVT and treated accordingly. Templates can be selected or discarded based a variety of factors including conditions in the patient or characteristics of arrhythmias.

In an example, a template is a sampled data representation of a heart depolarization. In another example, a template is a set of selected features from a sampled data representation of a heart depolarization. In another example a template is generated from multiple SVT beats, for example by taking an average of several beats.

Figure 1:
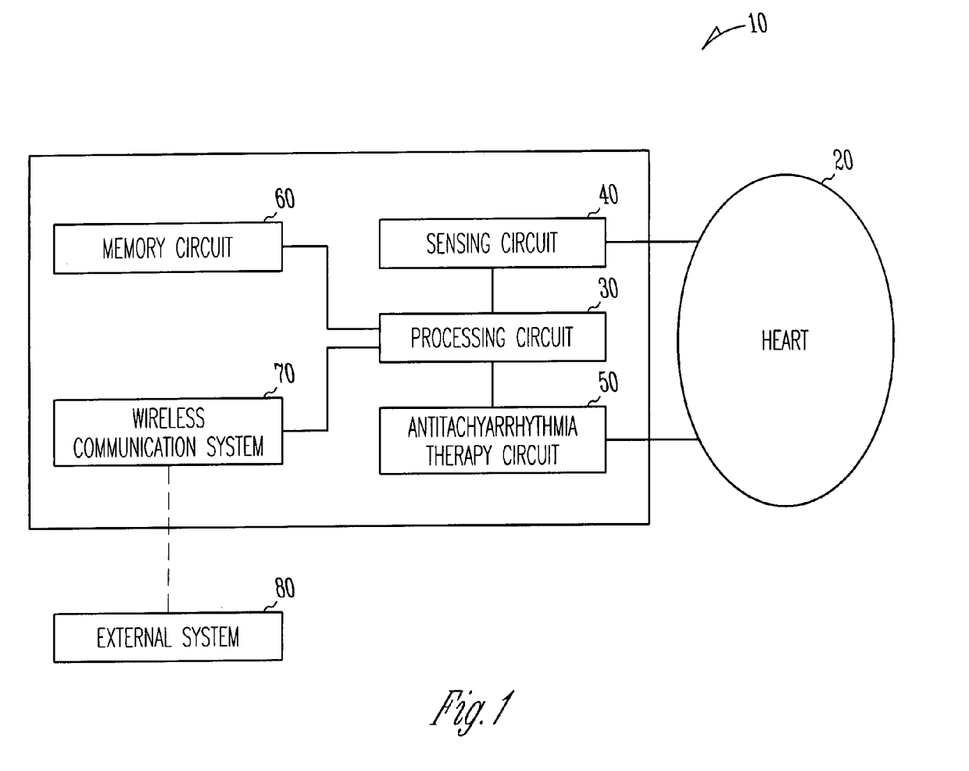
FIG. 1 is a schematic illustration of medical device and a heart.

FIG. 1 shows a schematic illustration of an exemplary medical device 10 and a heart 20. A processing circuit 30 communicates with a sensing circuit 40 and an antitachyarrhythmia therapy circuit 50. The sensing circuit 40 detects an intrinsic electrical signal from a heart. The antitachyarrhythmia therapy circuit 50 delivers defibrillation or other antitachyarrhythmia therapy to the heart 20. The processing circuit 30 analyzes input from the sensing circuit 40 and directs the antitachyarrhythmia therapy circuit 50 to administer antitachyarrhythmia therapy as necessary. The processing circuit 30 also sends information to a memory circuit 60.

The memory circuit 60 includes a storage medium, such as solid state RAM. In an exemplary configuration, the processing circuit 30 sends data received from the sensing circuit 40 during a tachyarrhythmia episode to the memory circuit 60 and the memory circuit 60 stores the data for later reference. The processing circuit 30 also communicates with a wireless communication system 70. The wireless communication system 70 sends data to or receives data from an external system 80, which typically includes a display system on which a user can view a graphical representation of the data. The medical device 10 can be configured as an implantable device, but is not necessarily implantable. While one processing circuit is shown, examples of the medical device including multiple processors are also possible. In varying examples, the processor is in a device implanted in the patient, or in a device such that is external to the patient, such as a programmer or a remote computer system.

Figure 2A:
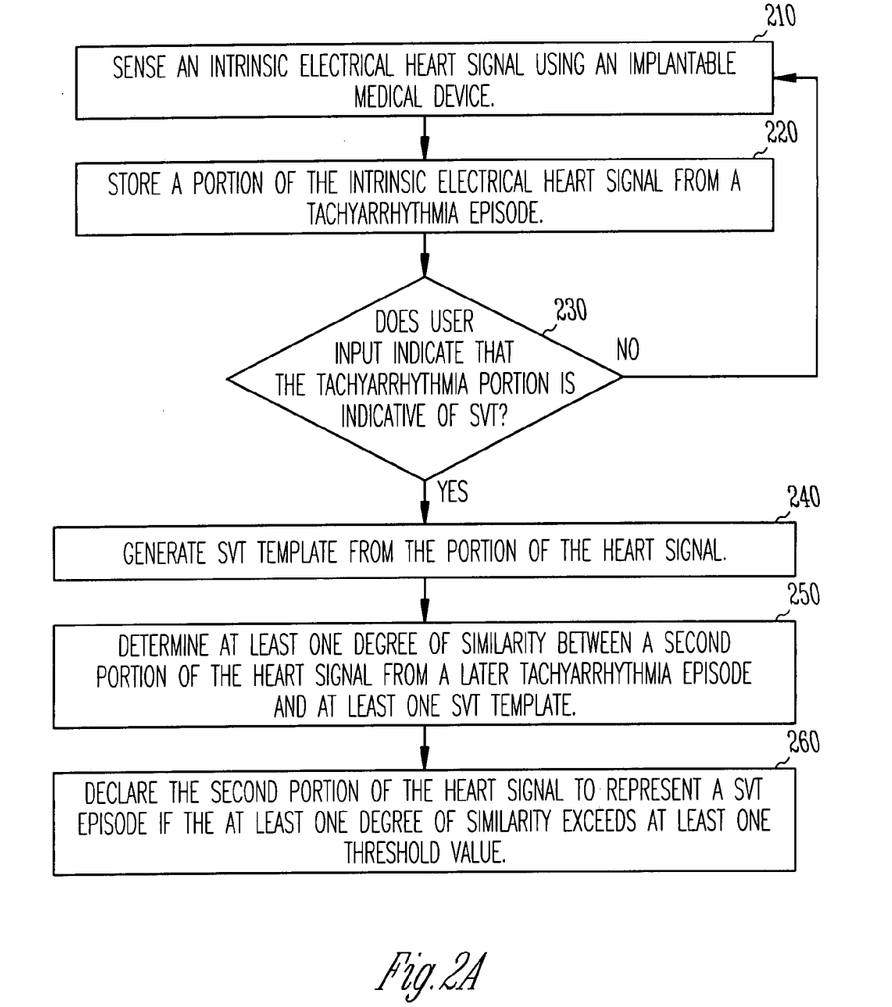
FIG. 2A is a flow chart that illustrates a process in which a degree of similarity is determined between a SVT template and a heart signal.

FIG. 2A is a flow chart that illustrates a process in which a SVT episode is identified and declared. At 210, an implantable medical device senses an intrinsic heart signal. At 220, the medical device stores a portion of the intrinsic electrical heart signal that was sensed during a tachyarrhythmia episode. At 230, a user indicates whether the portion of the intrinsic electrical heart signal is considered to be indicative of a SVT. In an alternative embodiment, a processor analyzes the portion of the signal to determine whether it is indicative of a SVT. If the portion of the intrinsic electrical heart signal is determined to be indicative of a SVT, a SVT template is generated at 240. In an example, a processor in the implanted medical device generates the template. In another example, the template is generated on an external computer system and downloaded to the implanted medical device. Various techniques can be used to generate the template. In an example, the template consists of one heart beat from the SVT episode. Alternatively, the template includes more than one heart beat. In an example, the template consists of the actual data from the intrinsic electrical heart signal as the template. Alternatively, a processor converts the intrinsic electrical heart signal data into a file that requires less storage space than the original data.

Returning to FIG. 2A, at 250, a processor determines at least one degree of similarity between a second portion of the heart signal from a later tachyarrhythmia episode and at least one SVT template. The degree of similarity is a quantity that is computed through an algorithm that uses the sensed intrinsic electrical heart signal (or a derivative thereof) as an input. In varying examples, determining the degree of similarity includes computing a feature correlation coefficient, a wavelet coefficient, or areas or integrals of a heart signal waveform or an approximation thereof. In varying examples, determining the degree of similarity involves computation of data in the time domain, wavelet domain, frequency domain, or other domains.

At 260, the device declares the second portion of the heart signal to represent a SVT episode if the degree of similarity exceeds a threshold valued. In one example, a processor in the medical device declares a SVT episode if a feature correlation coefficient for a heart beat exceeds a threshold. In another example, a processor declares a SVT if multiple feature correlation coefficients for respective multiple beats exceed a threshold value. In one scenario, a SVT is declared if a specified fraction of heart beats in a sequence of beats (e.g. 3 out of 10 beats) exhibit a feature correlation coefficient that exceeds a threshold. In another example, a SVT is declared if an average feature correlation coefficient for a number of beats exceeds a threshold (e.g. the average for 10 beats $\geq 0.94$).

In an example, the processor determines a degree of similarity between the second portion and multiple SVT templates. In one example, the processor begins determining degrees of similarity for the second portion for a sequence of templates and stops determining the degree of similarity if the degree of similarity for one of the templates exceeds a threshold. In other words, the processor compares the heart signal to a sequence of templates until a template match is found or all the templates are used. In another example, the portion of the heart signal is compared to all of the templates regardless of whether a match is found, and an SVT is declared if the degree of similarity for any one of the templates exceeds a threshold.

In addition to supraventricular tachyarrhythmia (SVT) episodes, a heart can exhibit other types of tachyarrhythmia that do not warrant antitachyarrhythmia therapy, including some instances ventricular tachyarrhythmia (VT). Such other non-lethal VT episodes can also be identified and used to generate templates.

Figure 2B:
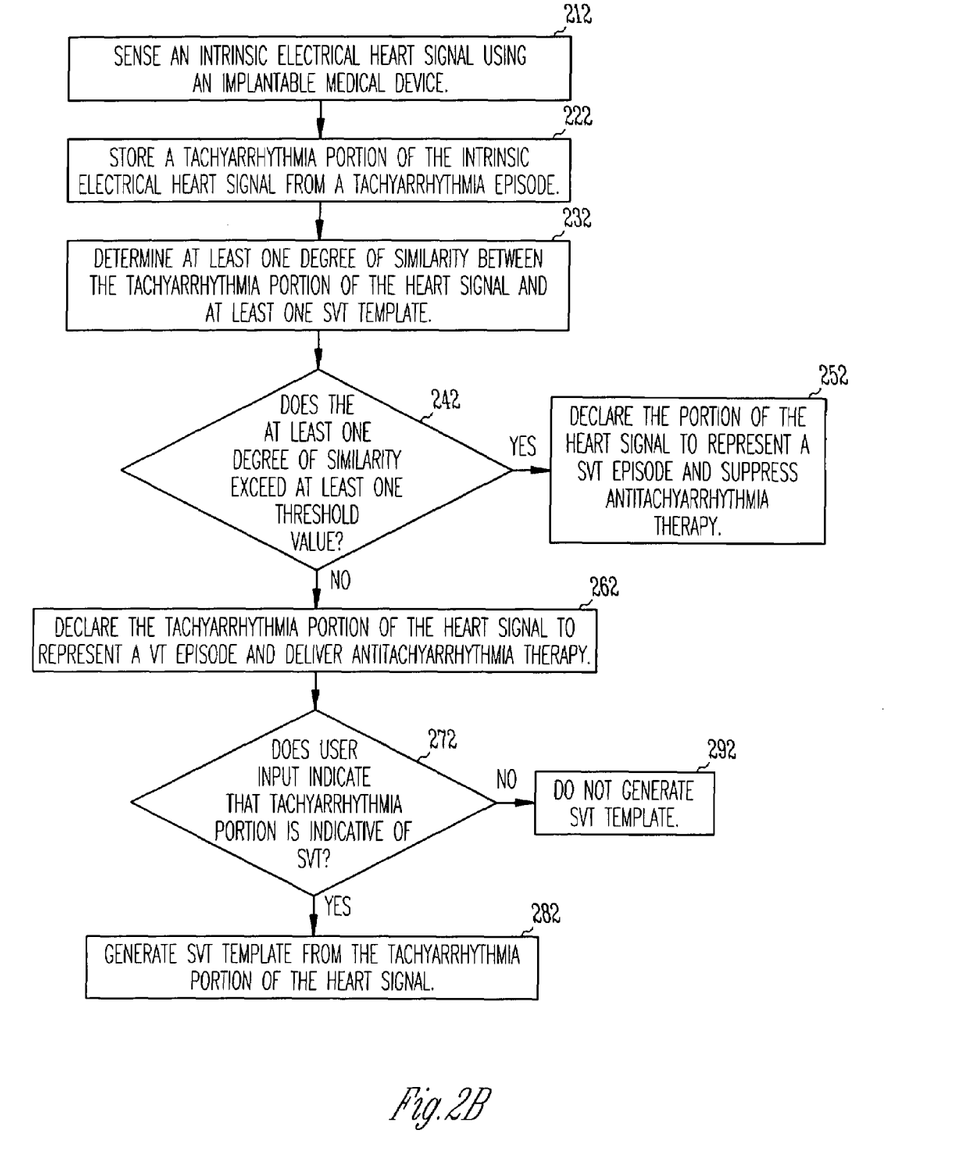
FIG. 2B is a flow chart that illustrates a process in which a degree of similarity is determined between a SVT template and a heart signal.

FIG. 2B is another flow chart that illustrates a process in which a degree of similarity is determined between a SVT template and a heart signal. At 212, an implantable medical device senses an intrinsic heart signal. At 222, the medical device stores a tachyarrhythmia portion of the intrinsic electrical heart signal that was sensed during a tachyarrhythmia episode. At 232, a processor determines at least one degree of similarity between the tachyarrhythmia portion of the heart signal and at least one SVT template. At 242, the processor determines whether the at least one degree of similarity exceeds at least one threshold value. In an example, the processor determines degrees of similarity for multiple beats and determines whether the degree of similarity exceeds a threshold for at least a predetermined fraction of the beats (e.g. 3 out of 8 beats). If the at least one degree of similarity exceeds at least one threshold value, the portion of the heart signal is declared to represent a SVT episode and antitachyarrhythmia therapy is suppressed, at 252. If the at least one degree of similarity does not exceed at least one threshold value (e.g. fewer than 3 out of 10 beats exhibit a degree of similarity in excess of a threshold), the portion of the heart signal is declared to represent a VT episode and antitachyarrhythmia therapy is delivered, at 262. The portion of the heart signal is stored and later presented to a user. If, at 272, an input from the user indicates that the portion is indicative of SVT, an SVT template is generated at 282. If another tachyarrhythmia event occurs, the process returns to box 232 and determines at least one degree of similarity between the tachyarrhythmia portion of the heart signal from the next tachyarrhythmia event and at least one SVT template, which can be the template generated at 282. If the user input does not indicate that the portion is indicative of SVT, a template is not generated, at 292.

Figure 2C:
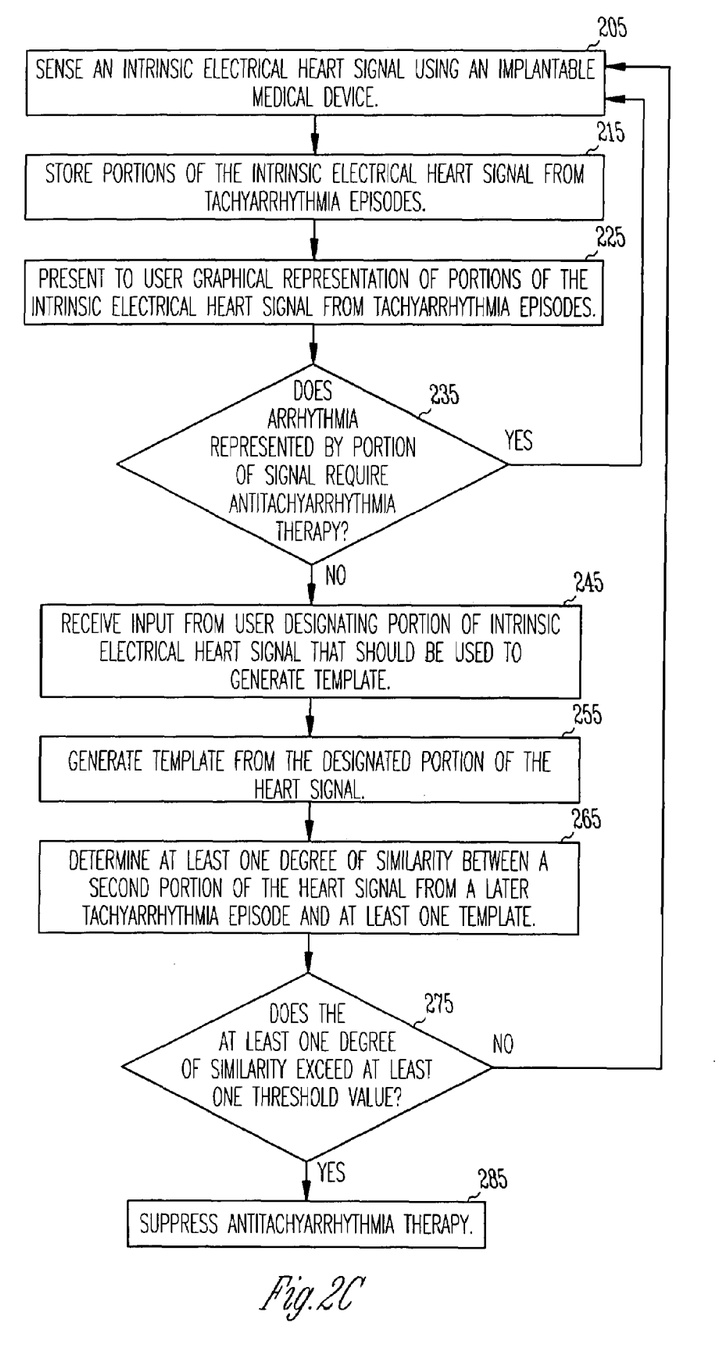
FIG. 2C is a flow chart that illustrates a process in which a template is generated for an arrhythmia morphology that does not require antitachyarrhythmia therapy.

FIG. 2C is a flow chart that illustrates a process in which a template is generated for an arrhythmia morphology that does not require antitachyarrhythmia therapy. At 205, an implantable medical device senses an intrinsic heart signal. At 215, the medical device stores one or more portions of the intrinsic electrical heart signal that were sensed during a tachyarrhythmia episode. At 225, a graphical representation of one or more stored portions of the intrinsic electrical heart signal is presented to a user. At 235, the user provides input that identifies at least one tachyarrhythmic portion of the intrinsic electrical heart signal that did not require antitachyarrhythmia therapy. The portion of the intrinsic electrical heart signal that did not require antitachyarrhythmia therapy can be, but is not necessarily, indicative of SVT. At 245, input is received from a user designating at least one portion of the intrinsic electrical heart signal that should be used to generate a template. At 255, a template is generated from a portion of the heart signal designated by the user. In an embodiment, an external computer system receives the input from the user to generate the template, which is downloaded to the implantable medical device. In another example, the user communicates directly with the implantable medical device, which generates the template. In an example, the user designates multiple portions of the heart signal, and multiple templates are generated.

Referring again to FIG. 2C, At 265, a processor in the medical device determines one or more degrees of similarity between a second portion of the intrinsic electrical heart signal from a later tachyarrhythmia episode and the template. At 275, the processor determines whether the one or more degrees of similarity exceed a threshold value. If the one or more degrees of similarity exceed a threshold value, the processor suppresses an antitachyarrhythmia therapy at 285.

In an alternative embodiment, in lieu of presenting a graphical representation to a user and receiving an input, a portion of the heart signal is analyzed automatically by a processor to determine whether antitachyarrhythmia therapy is appropriate.

Figure 3:
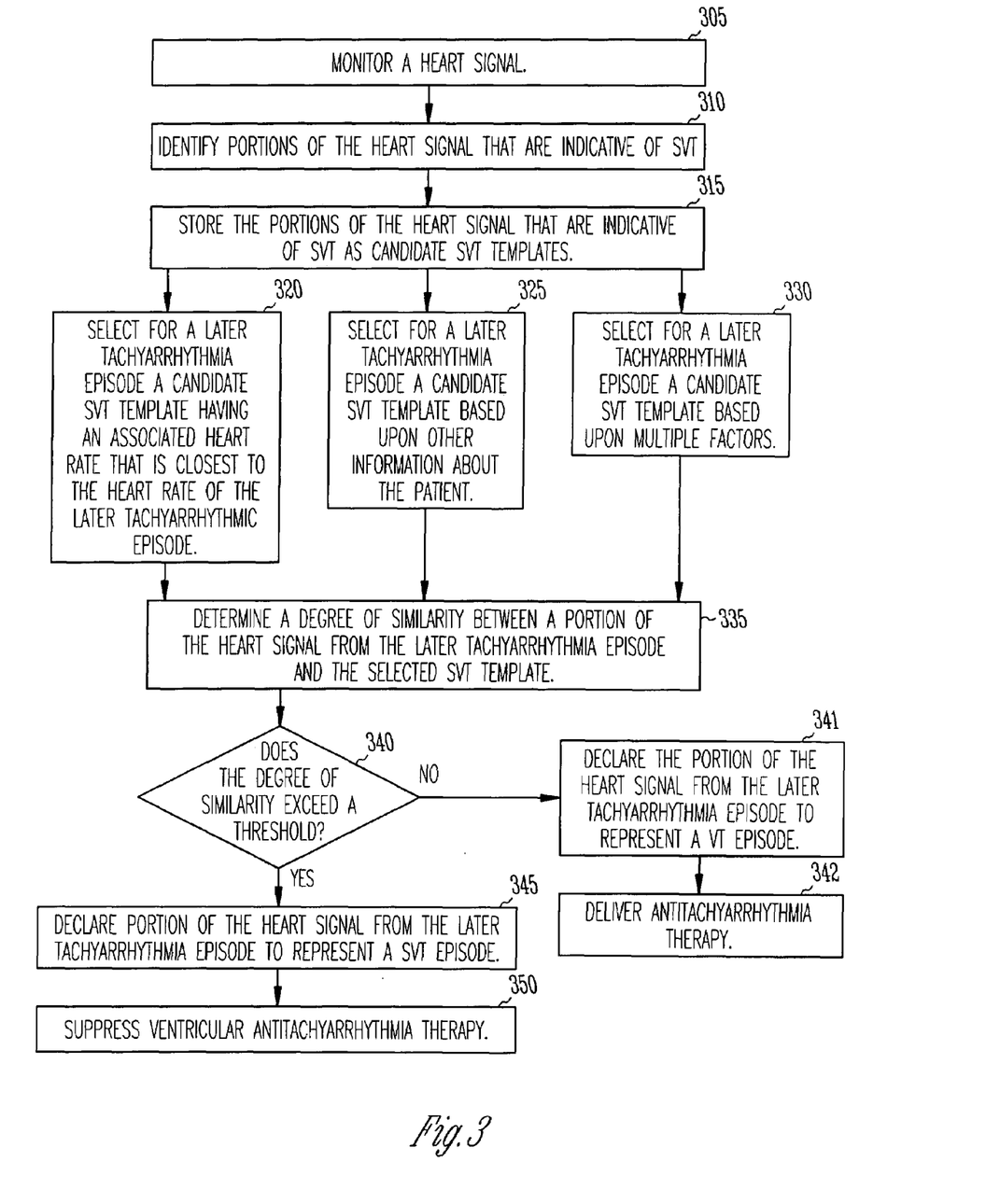
FIG. 3 is a flow chart that illustrates a method in which a degree of similarity is determined between a monitored heart signal and a SVT template selected from a group of candidate SVT templates.

FIG. 3 is a flow chart that illustrates a method in which a degree of similarity is determined between a monitored heart signal and a SVT template selected from a group of candidate SVT templates. At 305, a medical device monitors a heart signal. At 310, portions of the heart signal that are indicative of SVT are identified. In varying examples, the portions that are indicative of SVT can be identified by a physician, for example, or identified by an automated computerized analysis. At 315, portions of the heart signal that are indicative of SVT are stored as candidate SVT templates. The candidate template can be stored with a corresponding heart rate at which the template was observed. One or more selection protocols can be used to select a SVT template from a group of candidate SVT templates when analyzing a later tachyarrhythmia episode. For example, at 320, a SVT template is selected from a group of candidate templates based upon the heart rate associated with the candidate templates. The processor selects a template having a heart rate that is closest to the heart rate of the later tachyarrhythmia episode.

Alternatively, at 325, a candidate SVT template is selected based other information about the patient. In an example, the drug treatment regimen of a patient is considered in the selection of a SVT template. The morphology of SVT episodes in a patient can vary depending upon the drug treatment regimen of the patient. In one example, the medical device stores information about drug treatment regimens associated with the tachyarrhythmia episodes used to generate the candidate templates. The current drug regimen is also stored in the device. The processor selects a SVT template based upon a similarity between the drug treatment associated with the selected template and the current drug treatment. In another example, the medical device detects one or more of neural activity, patient activity, sleep state, hemodynamic status, transthoracic impedance, or cardiac impedance. In further examples, the device detects REM (random eye movement) status, sympathetic/parasympathetic tone, intercardiac blood pressure including right ventricular pressure, left atrial pressure, or pulmonary artery pressure, oxygen saturation, heart size and contractability, blood flow, or edema. In varying examples, the medical device considers one or more of these parameters in selecting an SVT template. In another example, the processor identifies one or more characteristics of the patient, and selects a SVT template using statistics from other patients having similar characteristics. In varying examples, the characteristics include (but are not limited to) as height, weight, age, disease history, medication, and patient status (such as neural activity, blood pressure, etc.)

In another alternative, at 330, a candidate SVT template is selected based upon multiple factors. In an example, both the heart rate and the drug treatment regimen are taken into consideration.

At 335, the processor determines a degree of similarity between the heart signal from the later tachyarrhythmia episode and the selected SVT template. The processor compares the degree of similarity to at least one threshold, at 340. If the degree of similarity falls below a threshold, a SVT episode is not declared. In an example, if a SVT episode is not declared, the medical device declares a VT episode at 341 and delivers a ventricular antitachyarrhythmia therapy at 342. Alternatively, other determinations can be made before the medical device administers ventricular antitachyarrhythmia therapy.

If the degree of similarity does exceed a threshold, the medical device declares the heart signal from the later tachyarrhythmia episode to represent a SVT episode at 345. The medical device then suppresses ventricular antitachyarrhythmia therapy at 350.

Figure 4:
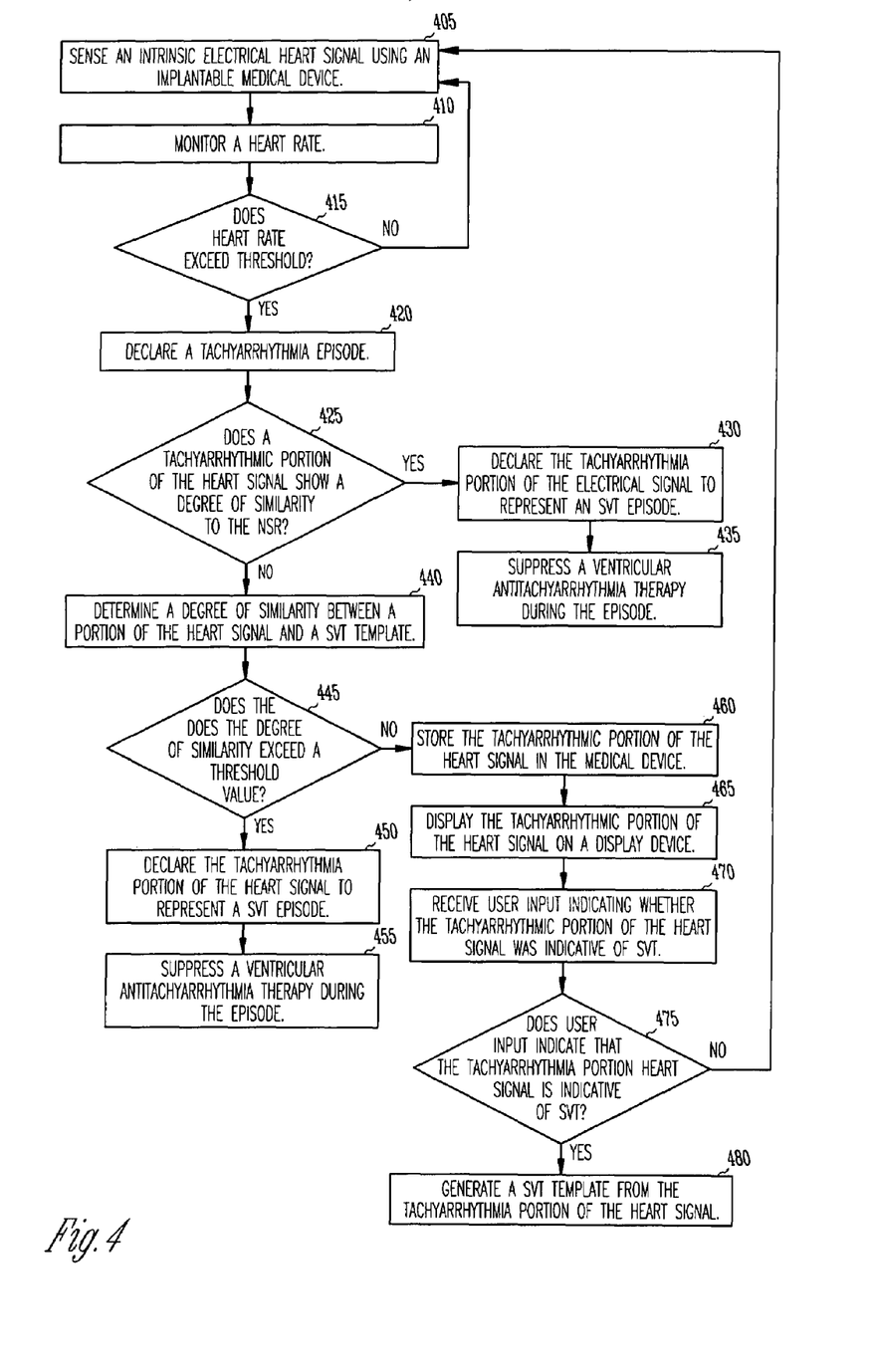
FIG. 4 is a flow chart that illustrates a method in which a heart signal is compared to a normal sinus rhythm and a SVT template.

FIG. 4 is a flow chart that illustrates a method in which a heart signal from a tachyarrhythmia episode is compared to a normal sinus rhythm and to a SVT template. At 405, a medical device senses an intrinsic electrical heart signal. The medical device monitors the heart rate at 410. At 415, the medical device compares the heart rate to a threshold. If the heart rate does not exceed the threshold, the medical device continues sensing the heart signal but does not perform a tachyarrhythmia discrimination algorithm. If the heart rate does exceed a threshold, the medical device declares a tachyarrhythmia episode at 420. At 425, the medical device compares the tachyarrhythmia portion of the heart signal to the normal sinus rhythm (NSR) template for the patient. In an example, the medical device computes a feature correlation coefficient between the tachyarrhythmia portion of the heart signal and the NSR template. If the tachyarrhythmia portion of the heart signal sufficiently correlates with the NSR template (e.g. the feature correlation coefficient exceeds a threshold), the medical device declares the tachyarrhythmia portion of the heart signal to represent a SVT episode at 430 and suppresses a ventricular antitachyarrhythmia therapy during the episode, at 435.

If the tachyarrhythmia portion of the heart signal is not similar to the NSR template, at 440 the medical device determines a degree of similarity between a portion of the heart signal and a SVT template. At 445, the medical device determines whether the degree of similarity exceeds a threshold. If the degree of similarity exceeds a threshold, the medical device declares the portion of the heart signal to represent a SVT episode at 450. In an example, declaring the portion of the heart signal to represent a SVT episode merely means making a determination to executing a response that is consistent with a SVT, such as suppressing a ventricular antitachyarrhythmia episode at 455.

If, at 445, the degree of similarity does not exceed a threshold, the medical device stores the tachyarrhythmia portion of the heart signal at 460. The stored portion is displayed to a user at 465 and an input is received from the user at 470. At 475, if the user indicates that the heart signal is indicative of SVT, a template is generated from the tachyarrhythmia portion of the heart signal, at 480.

Figure 5:
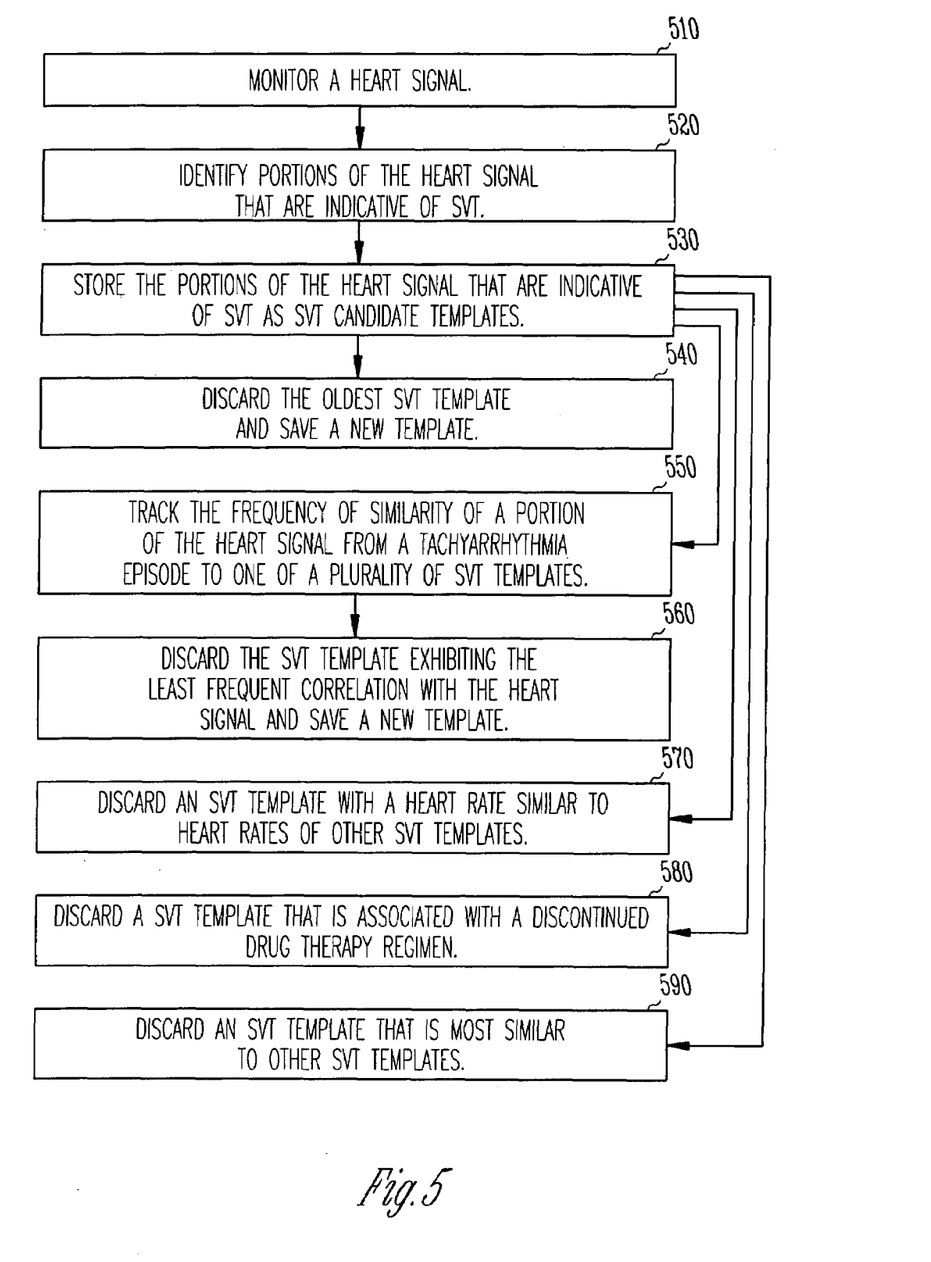
FIG. 5 is a flow chart that illustrates methods by which a SVT template is discarded from a storage medium and a new SVT template is added.

FIG. 5 is a flow chart that illustrates examples of methods by which a SVT template is added and an old SVT template is discarded. A medical device monitors a heart signal at 510. Portions of the heart signal that are indicative of SVT are identified at 520 through computer analysis or input from a user. The medical device stores the portions of the heart signal that are indicative of SVT as SVT candidate templates at 530. At 540, the medical device discards the oldest SVT template. Alternatively, the medical device tracks the frequency of similarity of a portion of the heart signal from a tachyarrhythmia episode to one of a plurality of SVT templates at 550 and discards the SVT template exhibiting the least frequent similarity with the heart signal and saves a new template at 560. In another alternative example, the medical device discards a SVT template with a heart rate similar to heart rates of other SVT templates at 570. In the example at 580, the medical device discards a SVT template that is associated with a discontinued drug therapy regimen. In the example at 590, the medical device discards a SVT template that is most correlated to other SVT templates. In varying examples, a decision of which template to discard is made by a computer system, the medical device, or a user who inputs a direction to discard a template.

Figure 6:
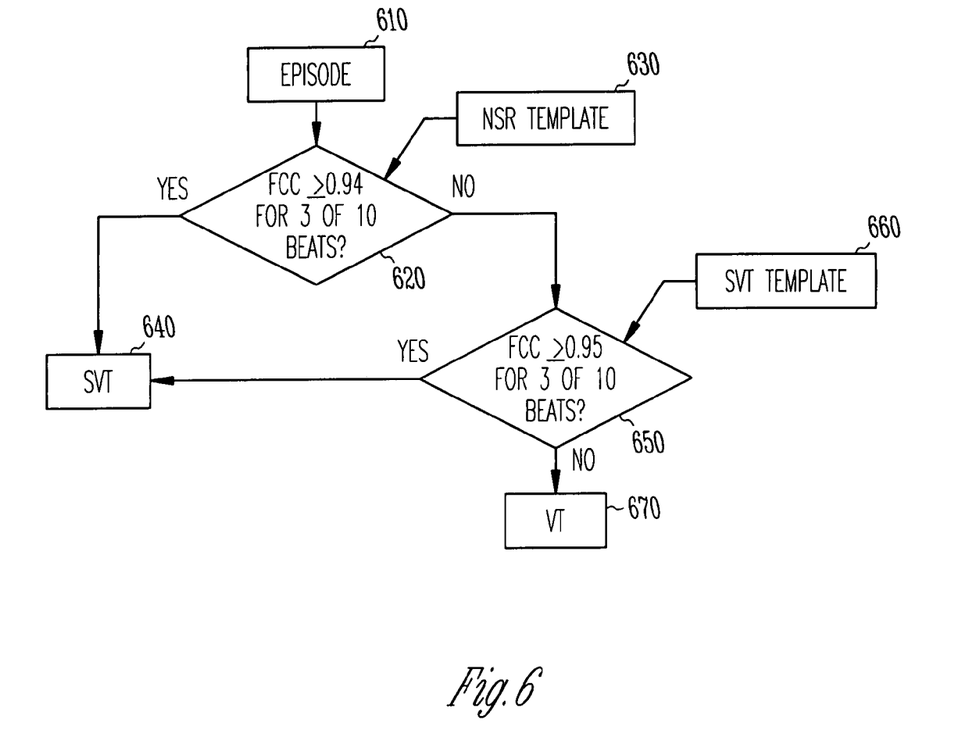
FIG. 6 is a flow chart that illustrates an embodiment of a process in which a heart signal from a tachyarrhythmia episode is compared to a normal sinus rhythm (NSR) template and then compared to a supraventricular tachyarrhythmia (SVT) template.

FIG. 6 is a flow chart that illustrates an example of a process in which a heart signal from a tachyarrhythmia episode is compared against a normal sinus rhythm (NSR) template 630 and then a supraventricular tachyarrhythmia (SVT) template 660. At 610, a tachyarrhythmia episode is detected. A NSR correlation module 620 computes a NSR feature correlation coefficient (FCC) for 10 heart beats. If the NSR feature correlation coefficient is equal to or greater than 0.94 for 3 out of 10 beats, the correlation module 620 declares a SVT and a SVT protocol 640 is followed. If the fewer than 3 out of 10 beats have a NSR feature correlation coefficient greater than or equal to 0.94, a SVT correlation module 650 computes a SVT feature correlation coefficient for the 10 heart beats. If the SVT feature correlation coefficient is equal to or greater than 0.95 for 3 out of 10 beats, the SVT correlation module 650 declares a SVT. If fewer than 3 out of 10 beats have a SVT feature correlation coefficient equal or greater than 0.95, the episode is treated as a ventricular tachyarrhythmia (VT) and a VT protocol is followed. For example, VT protocol 670 can include administration of antitachyarrhythmia therapy.

Figure 7:
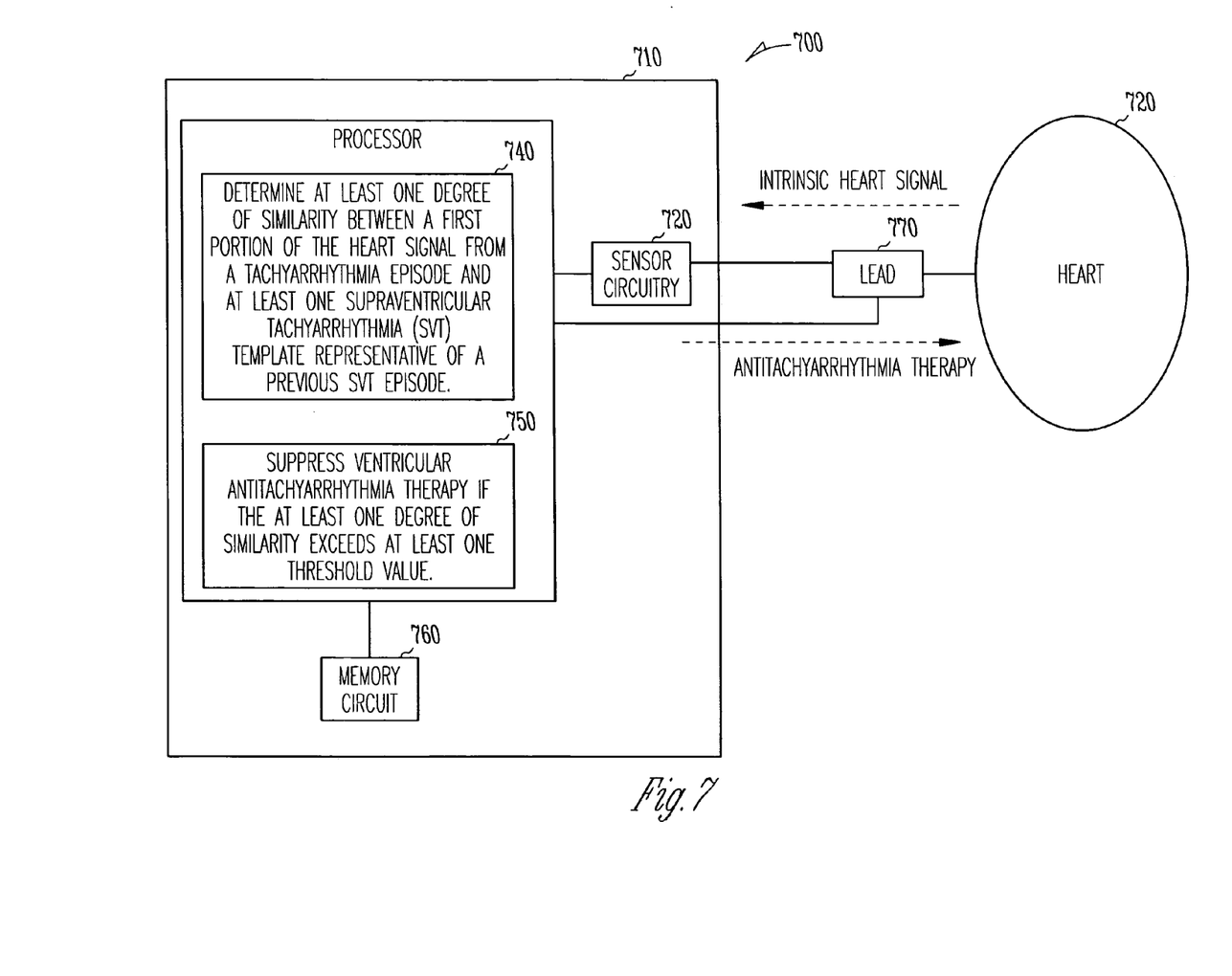
FIG. 7 is a block diagram of an implantable device.

FIG. 7 is a block diagram of an exemplary implantable device 700 incorporating a processor 710 and that runs software modules to analyze a signal from a heart 720 through a lead 770. A sensor 720 detects an intrinsic electrical heart signal. The processor 710 receives the signal from the sensor 720 and interprets the signal to determine whether an antitachyarrhythmia therapy should be delivered. A similarity module 740 determines a degree of similarity between portion of the heart signal from a tachyarrhythmia episode and a SVT template representative of a previous SVT episode. A suppress therapy module 750 suppresses a ventricular antitachyarrhythmia therapy if the degree of similarity exceeds a threshold value. SVT templates are stored in a memory circuit 760. A lead 770 delivers ventricular antitachyarrhythmia therapy as directed by the processor.

While the present examples have generally been described in terms of an implanted or implantable device, the presently described examples can also be implemented in non-implantable devices and systems.

Figure 8:
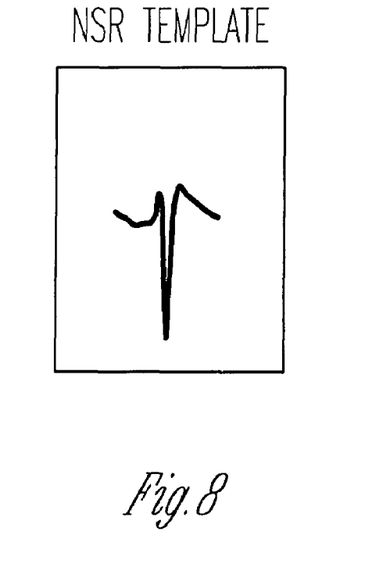
FIG. 8 shows an example of a normal sinus rhythm morphology.
Figure 9:
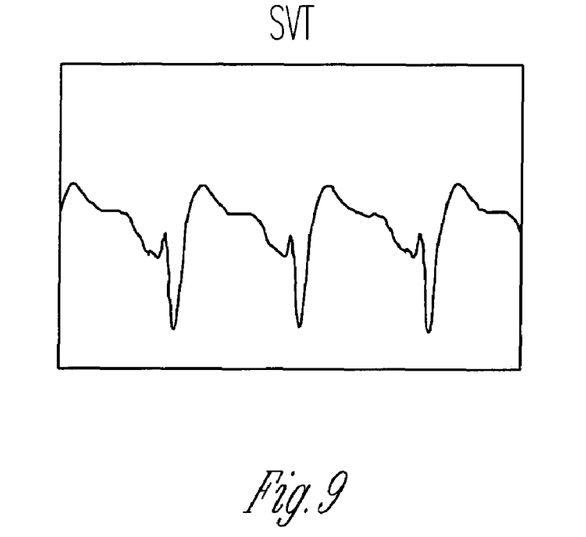
FIG. 9 shows an example of a SVT morphology.

FIG. 8 shows an example of a normal sinus rhythm morphology. FIG. 9 shows an example of a SVT morphology. In an example, a template includes a morphology for a single beat, as shown in FIG. 8. In another example, a template includes multiple beats, as shown if FIG. 9. In another example, a template for an atrial tachyarrhythmia can be created. The atrial tachyarrhythmia template can be used to declare a future episode of atrial tachyarrhythmia and suppress antitachyarrhythmia therapy as appropriate.

Varying algorithms can be used to generate a template and determine the degree of similarity between a heart signal and a template. In one example, a set of pre-determined rules are used to locate a number of points on a waveform, and those points are used as the template for comparison against a heart signal. In an example, eight pre-determined points can be located. In one example, the maxima, minima, and inflection points are located. The located points are stored as the template. Features are extracted from a portion of the heart signal by aligning the portion of the heart signal with the template. In an example, a peak on the template is aligned with a peak on the portion of the heart signal from one beat of a tachyarrhythmia episode. The amplitude of the points on the portion of the heart signal is measured at times corresponding to the points in the template. To determine the degree of similarity, a feature correlation coefficient (FCC) is computed using the amplitudes measured from the signal and the amplitude in the template. Computation of the feature correlation coefficient is further described in U.S. Pat. No. 6,708,058, which is incorporated herein by reference in its entirety.

In an example, a cardiac rate channel signal and a shock channel signal are sensed. The rate channel signal is measured from a sensing tip to a distal coil on a lead. The shock channel is measured from a distal coil to a proximal coil of the RV lead. A fiducial point is determined from the cardiac rate channel signals. A shock channel signal is aligned using the fiducial point. A template is generated using the aligned shock channel signal. Use of signals from rate and shock channels is further described in U.S. Pat. No. 6,708,058, which is incorporated by reference in its entirety. In other examples, a signal is sensed and then aligned using the same channel from which it was sensed.

In another example, a processor computes a wavelet transform or Fourier transform of the signal from which a template is to be generated. A predetermined number of largest wavelet coefficients are saved as a template. Features are extracted from a heart signal by aligning the peak of the signal with the peak of the template and computing the wavelet transform of the aligned tachy beat waveform. A predetermined number of largest wavelet coefficients are saved. The sum of the absolute value of the differences between the saved wavelet coefficients and the wavelet coefficients in the template is determined and divided by the sum of absolute value of the wavelet coefficients in the template. The resulting value is subtracted from 1 and multiplied by 100 to provide a "percent match score", which is compared to a threshold. In an example, the threshold is 70%, and beats having a percent match score greater than or equal to 70% are considered SVT in origin. In an example, if 3 out of 8 beats are SVT, an SVT episode is declared. Wavelet-based algorithms are further discussed in U.S. Pat. Nos. 6,393,316 and 5,782,888, which are incorporated herein by reference in their entirety.

In another example, a heart signal waveform is approximated as three consecutive triangles. The areas of each of the triangles is calculated and saved in a template. To extract features from a portion of a heart signal, peaks in the heart signal are aligned with the template, and the heart signal is approximated as three triangles. The area of each of the three triangles is calculated. To determine the degree of similarity to the template, a "similarity score" is determined based on the sum of the differences in the areas of the signal triangles and the template triangle. The similarity score is inversely proportional to this sum. If the similarity score is greater than a threshold, the beat is considered SVT in origin. If a predetermined number of beats exceed a threshold, an SVT episode is declared.

The preceding descriptions of techniques for determining a degree of similarity are considered exemplary. Other techniques, or variations of the described techniques, can be employed with the methods described in this application.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A machine-assisted method comprising:
   sensing an intrinsic electrical heart signal using an implantable medical device;
   detecting a first tachyarrhythmia episode using the intrinsic electrical heart signal;
   selecting a first tachyarrhythmia template from a group of two or more candidate supraventricular tachyarrhythmia (SVT) templates;
   comparing at least a portion of the intrinsic electrical heart signal obtained during the first tachyarrhythmia episode to the selected first tachyarrhythmia template, the first tachyarrhythmia template representative of a signal morphology of a first type of tachyarrhythmia; and
   declaring whether the detected first tachyarrhythmia episode constitutes the first type of tachyarrhythmia based on the comparison.

2. The method of claim 1, wherein:
   the comparing comprises determining at least one degree of similarity between the intrinsic electrical heart signal during the first tachyarrhythmia episode and the first tachyarrhythmia template; and
   the declaring comprises declaring the first tachyarrhythmia episode to be a supraventricular tachyarrhythmia (SVT) episode if the at least one degree of similarity exceeds at least one threshold value.

3. The method of claim 1, comprising:
   detecting a second tachyarrhythmia episode using the intrinsic electrical heart signal;
   storing at least part of the intrinsic electrical heart signal during the second tachyarrhythmia episode;
   receiving user input declaring the intrinsic electrical heart signal during the second tachyarrhythmia episode to be indicative of the first tachyarrhythmia type, wherein the first tachyarrhythmia type comprises a supraventricular tachyarrhythmia (SVT); and
   generating the first tachyarrhythmia template using the intrinsic electrical heart signal during the second tachyarrhythmia episode that was declared by the user input to be indicative of the first tachyarrhythmia type.

4. The method of claim 3, further comprising:
   presenting at least a portion of the intrinsic electrical heart signal obtained during the second tachyarrhythmia episode to a user; and
   receiving from the user input indicating a segment of the intrinsic electrical heart signal obtained during the second tachyarrhythmia episode to be used to generate the first tachyarrhythmia template.

5. The method of claim 4, further comprising:
   presenting a plurality of portions of the intrinsic electrical heart signal corresponding to a plurality of tachyarrhythmia episodes to a user; and
   receiving from the user input indicating which of the plurality of portions of the intrinsic electrical signal are to be used to generate one or more first tachyarrhythmia templates.

6. The method of claim 1, further comprising suppressing a ventricular tachyarrhythmia therapy during the first tachyarrhythmia episode of the first type of tachyarrhythmia.

7. The method of claim 1, wherein the selecting the first tachyarrhythmia template from a group of two or more candidate supraventricular tachyarrhythmia (SVT) templates comprises receiving user input and using information from the user input for performing the selecting.

8. The method of claim 1, wherein the detecting the first tachyarrhythmia episode comprises:
monitoring a heart rate; and
when the heart rate exceeds a tachyarrhythmia rate threshold, declaring a detection of the first tachyarrhythmia episode.

9. The method of claim 8, further comprising:
comparing a portion of the intrinsic electrical heart signal obtained during the first tachyarrhythmia episode with a normal sinus rhythm (NSR) template; and
when a second portion of the electrical signal sufficiently correlates to the NSR template, declaring the first tachyarrhythmia episode to be a SVT episode and suppressing a ventricular tachyarrhythmia therapy during the declared SVT episode.

10. The method of claim 1, comprising:
detecting a second tachyarrhythmia episode using the intrinsic electrical heart signal;
receiving user input declaring the second tachyarrhythmia episode to be of a type that does not require ventricular antitachyarrhythmia therapy;
generating the first tachyarrhythmia template from the intrinsic electrical heart signal obtained during the second tachyarrhythmia episode, wherein the first tachyarrhythmia template is representative of an intrinsic electrical heart signal that does not require ventricular anti-tachyarrhythmia therapy; and
suppressing a ventricular tachyarrhythmia therapy when the first tachyarrhythmia episode constitutes the first type of tachyarrhythmia, otherwise delivering a ventricular anti-tachyarrhythmia therapy in response to the first tachyarrhythmia therapy episode.

11. The method of claim 1, comprising:
monitoring information about a patient; and
using the information about the patient for selecting as the first tachyarrhythmia template at least one supraventricular tachyarrhythmia (SVT) template, the at least one SVT template selected from a group of two or more candidate SVT templates.

12. The method of claim 11, wherein each candidate SVT template is associated with a heart rate at which a prior tachyarrhythmia episode used to generate the SVT template was observed, and wherein the monitoring information includes monitoring a patient's heart rate and wherein the selecting the first tachyarrhythmia template includes selecting the candidate SVT template having an associated heart rate that is closest to the monitored heart rate.

13. The method of claim 12, in which selecting the first tachyarrhythmia template includes selecting as the first tachyarrhythmia template the candidate SVT template having an associated heart rate that is second closest to the heart rate of the first tachyarrhythmia episode.

14. The method of claim 11, wherein the comparing includes determining degrees of similarity between the portion of the intrinsic electrical heart signal obtained during the first tachyarrhythmia episode and multiple SVT templates.

15. The method of claim 11, comprising:
identifying at least one portion of the intrinsic electrical heart signal that is indicative of SVT; and
storing at least one portion of the intrinsic electrical heart signal that is indicative of SVT as a candidate SVT template.

16. The method of claim 15, wherein the storing includes discarding an older SVT template.

17. The method of claim 15, wherein the storing includes discarding a SVT template associated with a discontinued drug therapy regimen.

18. The method of claim 15, wherein the storing includes receiving an input from a user designating a SVT template to be discarded, and discarding the designated SVT template.

19. The method of claim 15, further comprising tracking the degree of similarity of the intrinsic electrical heart signal from the first tachyarrhythmia episode to the candidate SVT templates, and discarding a candidate SVT template exhibiting the least frequent similarity with the intrinsic electrical heart signal during the first tachyarrhythmia episode.

20. The method of claim 15, wherein the storing includes discarding an SVT template with a heart rate similar to heart rates at which other SVT templates were identified.

21. The method of claim 15, wherein the storing includes discarding an SVT template that is most similar to other SVT templates.

22. The method of claim 11, wherein the comparing comprises determining at least one degree of similarity between a portion of the intrinsic electrical heart signal and the first tachyarrhythmia template, comprising:
determining at least one first degree of similarity between a portion of the intrinsic electrical heart signal from the first tachyarrhythmia episode and a first SVT template; and
when the first degree of similarity does not exceed a threshold, determining at least one second degree of similarity between the portion of the intrinsic electrical heart signal from the first tachyarrhythmia episode and a second SVT template.

23. The method of claim 11, wherein the monitoring information about the patient includes monitoring at least one of the patient's neural activity, sleep state, hemodynamic status, transthoracic impedance, and cardiac impedance.

24. The method of claim 1, comprising selecting the first tachyarrhythmia template from a group of candidate templates by comparing a current drug therapy regimen to drug therapy regimens associated with the respective candidate templates.

25. The method of claim 1, comprising:
comparing at least a portion of the intrinsic electrical heart signal obtained during the first tachyarrhythmia episode to a normal sinus rhythm (NSR) template and, if the portion of the intrinsic electrical heart signal during the first tachyarrhythmia episode is determined to be not sufficiently similar to the NSR template, then performing the comparing at least a portion of the intrinsic electrical heart signal obtained during the first tachyarrhythmia episode to the first tachyarrhythmia template, otherwise declaring that the first tachyarrhythmia episode constitutes the first type of tachyarrhythmia.

26. A machine-assisted method comprising:
sensing an intrinsic electrical heart signal using an implantable medical device;
detecting a first tachyarrhythmia episode using the intrinsic electrical heart signal;
comparing at least a portion of the intrinsic electrical heart signal obtained during the first tachyarrhythmia episode to a first tachyarrhythmia template, the first tachyarrhythmia template representative of a signal morphology of a first type of tachyarrhythmia, wherein the comparing comprises determining at least one degree of similarity between a portion of the intrinsic electrical heart signal and the first tachyarrhythmia template, including computing a feature correlation coefficient for each of a plurality of portions of the intrinsic electrical heart signal detected during the first tachyarrhythmia episode, and further comprising withholding treatment if at least a predetermined fraction of the feature correlation coefficients exceed a predetermined threshold, wherein the computing the feature correlation coefficient comprises computing a feature correlation coefficient for each of a plurality of sequential heart beats during the first tachyarrhythmia episode and wherein the predetermined fraction and the predetermined threshold are programmably selectable; and declaring whether the detected first tachyarrhythmia episode constitutes the first type of tachyarrhythmia based on the comparison.

27. The method of claim 26, comprising selecting the threshold using one or more statistics from other patients having one or more similar characteristics.

28. The method of claim 27, comprising selecting the threshold using information about one or more of the patient's age, disease history, and medication.

29. A system comprising:
an implantable sensor configured to sense an intrinsic electrical heart signal;
a tachyarrhythmia detector, coupled to the sensor, the tachyarrhythmia detector configured for detecting a first tachyarrhythmia episode using the intrinsic electrical heart signal;
a first tachyarrhythmia template, representative of a signal morphology of a first type of tachyarrhythmia;
a processor, coupled to the first tachyarrhythmia template and the tachyarrhythmia detector, the processor configured for comparing at least a portion of the intrinsic electrical heart signal obtained during the tachyarrhythmia episode to the first tachyarrhythmia template, the processor declaring whether the detected first tachyarrhythmia episode constitutes the first type of tachyarrhythmia based on the comparison, in which the processor is configured to determine whether anti-tachyarrhythmia therapy should be delivered in response to the first tachyarrhythmia episode by determining a heart rate from the intrinsic electrical heart signal, selecting as the first tachyarrhythmia template an SVT template having a heart rate that is closest to the heart rate of the intrinsic electrical heart signal, determining at least one degree of similarity between a portion of the intrinsic electrical heart signal and the first tachyarrhythmia template.

30. The system of claim 29, in which the processor is further configured to suppress a ventricular anti-tachyarrhythmia therapy if at least one degree of similarity between the intrinsic electrical heart signal and the first tachyarrhythmia template exceeds a threshold value.

31. The system of claim 29, wherein the processor is further configured to store in a memory as a candidate SVT template a portion of the intrinsic heart signal that is representative of a SVT episode.

32. The system of claim 31, wherein the processor is configured to discard an oldest candidate template from the memory to make room for a new SVT template.

33. The system of claim 31, wherein the processor is configured to discard an SVT template that has been least frequently selected.

34. The system of claim 29, comprising an anti-tachyarrhythmia therapy circuit configured to deliver ventricular anti-tachyarrhythmia therapy, and wherein the processor is configured to compare the intrinsic electrical heart signal during the first tachyarrhythmia episode to an NSR template that represents a normal sinus rhythm, and to suppress the ventricular anti-tachyarrhythmia therapy if at least one degree of similarity between the NSR template and the portion of the intrinsic electrical heart signal during the first tachyarrhythmia episode exceeds a threshold value.

35. The system of claim 29, comprising a memory circuit configured to store at least a portion of the intrinsic electrical heart signal obtained during the first tachyarrhythmia episode.

36. The system of claim 29, wherein at least a portion of the system is implantable, the system comprising a wireless communication circuit, wherein a recorded portion of the intrinsic electrical heart signal can be communicated to a non-implanted device through the wireless communication circuit.

37. The system of claim 36, wherein the non-implanted device includes a display that is configured to display a graphical representation of a recorded portion of the intrinsic heart signal to a user.

38. A system comprising:
means for sensing an intrinsic electrical heart signal using an implantable medical device;
means for detecting a first tachyarrhythmia episode using the intrinsic electrical heart signal;
means for selecting a first tachyarrhythmia template from a group of two or more candidate supraventricular tachyarrhythmia (SVT) templates;
means for comparing at least a portion of the intrinsic electrical heart signal obtained during the first tachyarrhythmia episode to the selected first tachyarrhythmia template, the first tachyarrhythmia template representative of a signal morphology of a first type of tachyarrhythmia; and
means for declaring whether the detected first tachyarrhythmia episode constitutes the first type of tachyarrhythmia based on the comparison.

* * * * *